(12) United States Patent
Molnar et al.

(10) Patent No.: US 6,231,783 B1
(45) Date of Patent: *May 15, 2001

(54) REPLACEMENT SOLVENTS FOR USE IN CHEMICAL SYNTHESIS

(75) Inventors: Linda K. Molnar, Philadelphia, PA (US); T. Alan Hatton, Sudbury; Stephen L. Buchwald, Newton, both of MA (US)

(73) Assignee: Massachusetts Institute of Technology, Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/748,457

(22) Filed: Nov. 13, 1996

Related U.S. Application Data

(60) Provisional application No. 60/006,728, filed on Nov. 14, 1995.

(51) Int. Cl.[7] .................................. C09K 3/00; B01F 1/00
(52) U.S. Cl. .................................. 252/182.3; 252/182.29; 252/364
(58) Field of Search .............................. 252/364, 182.29, 252/182.3; 510/506; 549/475, 497

(56) References Cited

U.S. PATENT DOCUMENTS

| | | |
|---|---|---|
| 2,040,898 | 5/1936 | Zelhoefer . |
| 2,945,994 | 7/1960 | Dazzi . |
| 2,993,915 | 7/1961 | Luskin . |
| 3,542,602 | 11/1970 | Gabano . |
| 3,668,134 | 6/1972 | Lamberti et al. . |
| 3,898,269 * | 8/1975 | Cohen et al. .................... 558/429 |
| 4,005,584 | 2/1977 | Li . |
| 4,072,027 | 2/1978 | Berenbaum et al. . |
| 4,367,343 * | 1/1983 | Tamborski et al. .................. 556/478 |
| 4,808,497 | 2/1989 | Blomgren et al. . |
| 5,039,758 | 8/1991 | Tobita et al. . |
| 5,231,153 | 7/1993 | Hsu et al. . |
| 5,448,003 * | 9/1995 | Hsu et al. ............................ 526/181 |
| 5,554,778 * | 9/1996 | Beatty et al. ........................... 556/21 |

FOREIGN PATENT DOCUMENTS

| | | |
|---|---|---|
| 2 000 771 | 1/1979 | (GB) . |
| 59-090846 | 5/1984 | (JP) . |
| 59-094764 | 9/1984 | (JP) . |
| 62-026763 | 7/1987 | (JP) . |
| 1-092223 | 7/1989 | (JP) . |

OTHER PUBLICATIONS

CA 111:81323t Pasquariello et al. "Practical rechargeable lithium batteries" *J. Power Sources* 26(1–2):247 (1989).

CA 80:16128k Komatsu et al. "Diene polymers" Japan Kokai 73 56,722 (Aug. 1973).

(List continued on next page.)

*Primary Examiner*—Joseph D. Anthony
(74) *Attorney, Agent, or Firm*—Choate, Hall & Stewart

(57) ABSTRACT

Replacement solvents for use in chemical synthesis include polymer-immobilized solvents having a flexible polymer backbone and a plurality of pendant groups attached onto the polymer backbone, the pendant groups comprising a flexible linking unit bound to the polymer backbone and to a terminal solvating moiety. The polymer-immobilized solvent may be dissolved in a benign medium. Replacement solvents for chemical reactions for which tetrahydrofuran or diethyl may be a solvent include substituted tetrahydrofurfuryl ethers and substituted tetrahydro-3-furan ethers. The replacement solvents may be readily recovered from the reaction train using conventional methods.

3 Claims, 7 Drawing Sheets

OTHER PUBLICATIONS

CA 121:178799x Miyamoto et al. "A new aerobic oxidation system using Pd–Cu catalysts in the presence of CO" *Chem. Lett.* 7:1149 (1994).

J.J. Sahbari "Safe Replacement Solvents and Alternative Technologies" Presentation at Incinerable Hazardous Waste Minimization Workshop, Jan. 14 and 15, 1991.

L.L. Chan and J. Smid "Contact and Solvent–Separated Ion Pairs of Carbanions. V. The Role of Solvent Structure in Alkali Ion Solvation" *J. Am. Chem. Soc.* 90(17): 4654 (Aug. 1968).

CA 113:58122j Pandey et al. "Photoinduced single electron trasfer initiated heterolytic carbon–selenium bond dissociation. Sequential one–pot selenylation and deselenylation reaction." *J. Am. Chem. Soc.* 112(14):5650 (1990).

* cited by examiner

REPLACEMENT SOLVENTS FOR USE IN CHEMICAL SYNTHESIS

This application claims priority under 35 U.S.C. 119(e) to provisional application No. 60/006,728 filed Nov. 14,1995.

This invention was made with support from the United States Government under Department of Energy Grant Contract No. DE-AC07-94ID13223. The government has certain rights in this invention.

FIELD OF THE INVENTION

The present invention relates to novel solvent systems for use in chemical and pharmaceutical synthesis. The invention more particularly relates to solvent systems having improved physical properties to minimize entry into the environment and to facilitate separations and cleaning operations to minimize pollution.

BACKGROUND OF THE INVENTION

Many of the chemical reaction and separation processes used in the pharmaceutical and fine chemicals industry require the use of organic solvents. These solvents are often volatile and sufficiently water-soluble to contaminate air emissions and aqueous discharge streams, adding to the environmental burden and the cost of downstream processing and recovery operations. Recognized hazardous industrial solvents include chlorinated hydrocarbons, such as methylene chloride, chloroform and carbon tetrachloride; aromatic hydrocarbons, such as benzene, toluene and xylene; ketones, such as acetone, methylethylketone (MEK) and methylisobutylketone (NUBK); and ethers, such as tetrahydrofuran (THF) and diethyl ether.

The use of tetrahydrofuran (THF) in pharmaceutical processing is problematic as the solvent is used for a range of reactions which must be carried out under anhydrous conditions, such as Grignard reactions. The desired product is often obtained by aqueous precipitation. Since THF is soluble in the water phase, it typically is recovered by distillation which leads to problems not only with the recovery of solvent, but also with the loss of anti-oxidants, such as BHT, which are added to arrest the potentially dangerous formation of peroxides. The volatility of the solvent can also lead to unwanted vapor emissions to the environment. In a typical reaction sequence using THF as the solvent, a reaction mixture is extracted with water to remove salts and polar substituents. This may cause some of the solvent to be dragged into the aqueous phase while the rest remains in the product phase. The solvent must then be recovered from the aqueous phase for recycling and to minimize loss to the environment. The product must then be isolated, which may involve a switch to a solvent in which the product will crystallize. Continuous switching of solvents is problematic in chemical synthesis because it is time-consuming, generates mixed solvent systems which must be separated, introduces potential pollutants which must be removed and produces large volumes of waste.

Another often used, but environmentally harmful, solvent is methylene chloride. Methylene chloride is used both as a reaction medium and for extractive separation processes. Equipment cleaning using solvents can also contribute to the environmental pollution problem.

In recent years, federal and state regulations have been passed which strongly discourage the use of solvents which are not environmentally benign. Of particularly strong impact is the Pollution Prevention Act passed by Congress in October 1990 and the Resource Conservation and Recovery Act of 1988. These laws strongly encourage hazardous waste minimization by recovery and recycling of organic solvents. Such a strategy is less expensive than collection, treating or disposal of hazardous wastes, and is also of much less risk to workers, the environment and the community. In addition, substitution of non-volatile organic compounds for the commonly used volatile solvents is strongly encouraged.

Owing to these laws and increased public awareness of the harm done by such solvents, there is considerable interest in ameliorating the deleterious environmental effects associated with solvent usage in pharmaceutical reaction processes. The different approaches that are being considered include (i) a search for new synthetic procedures that utilize less hazardous solvents, (ii) the establishment and exploitation of extensive computer data bases on solvents, (iii) the use of solvent mixtures to obtain the desired solvation properties, and (iv) the intelligent design of reaction/separation trains to minimize mixing of solvents in different operations, and thereby minimize the problems associated with their recovery and recycle. However, the development of new synthetic procedures may be at the expense of yield and productivity, and the time-frame for such developments is probably fairly long. Also, process modifications involving material substitution require complete approval (and in many cases preapproval if a drug is concerned) by the FDA before the new product can be marketed. This can be an expensive and time-consuming process, and may result in a temporary shutdown of production while necessary changes are being implemented.

It is therefore desirable to provide a solution to the problem which can be implemented in the short or intermediate term and which involves minimal alteration or disturbance to the current pharmaceutical processes. Use of environmentally more benign replacement solvents, combined with simplified recovery and recycling processes, is therefore particularly appealing. Current solvent recovery and recycling processes focus on distillation and various chromatography steps. Estimated savings due to recycling are in most cases offset by the cost of the recovery process equipment, still bottoms disposal and makeup for non-recovered solvent. It is thus desirable when selecting suitable replacement solvents that difficult separation problems be avoided, that more efficient recovery of solvents be facilitated, and appropriate solvation properties be attained while ensuring that the potential for environmental contaminations is minimized.

A synthetic route to n-alkyl tetrahydrofurfuryl ethers has been previously described. Kirner et al. *JACS* 1930 (52) :3251–3256 (1930). While the synthesis may be modified for the preparation of n-alkyl tetrahydro-3-furan ethers, no report of these compounds in the literature has been found. Various uses of alkyl tetrahydrofurfuryl ethers have been reported, including absorption refrigeration crease-proofing of cellulosic fabrics, in detergent compositions and as modifiers in the polymerization reactions of conjugated dienes. However, there has been no report on their use as a replacement solvent for THF in chemical and pharmaceutical reactions.

SUMMARY OF THE INVENTION

It is the object of the present invention to provide solvents of low volatility, suitable for replacing known solvents in pharmaceutical, chemical and industrial processes.

It is a further object of the invention to provide a solvent which will minimize entry of the solvent into the environment and may be recovered and recycled using readily available separations techniques.

It is a further object of the invention to provide a solvent for use in chemical reactions having a maximum working range between melting and boiling point, chemical and thermal stability in the working range, good solubility of reactants and products, compatibility with the analytical methods employed and a high degree of purity.

It is yet a further object of the invention to provide a solvent which will minimize or reduce switching of solvents during chemical processing.

The present invention provides a novel solvent system which retains the requisite solvation properties while at the same time renders the solvent environmentally friendly. The solvent of the present invention is desirably non-volatile, easily recovered from process streams and potentially reusable in situ. The solvents of the present invention include novel derivatives of currently used solvents in which solvation properties are retained, and yet they possess higher boiling points to reduce air emissions and are non-water soluble to minimize losses to effluent waste streams. The solvents of the present invention also include solvent molecules which have been immobilized by attachment to polymers, which can then be mixed in a benign continuous phase.

In one aspect of the invention, a polymer-immobilized solvent is provided which comprises a flexible polymer backbone; and a plurality of pendant groups attached onto the polymer backbone, the pendant groups comprising a flexible linking unit bound to the polymer backbone and to a terminal solvating moiety. In a preferred embodiment, a benign medium in which the polymer-immobilized solvent is soluble is added.

In another aspect of the invention, a solvent for use in reactions for which THF is used comprises a compound of the formula,

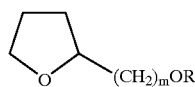

(I)

where R is selected from the group consisting of linear, branched and cyclic alkyl groups having between one and twenty carbons, aryl groups, alkylaryl groups and alkoxyl groups having up to 20 ether linkages and perferably up to 10 linkages, and where m=0–2. It is recognized that a higher values for m may impart similar properties to the molecule and is within contemplation of the present invention.

In another aspect of the invention, a solvent for use in reactions for which THF is used comprises a compound of the formula,

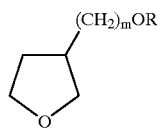

(II)

where R is selected from the group consisting of linear, branched and cyclic alkyl groups having between one and twenty carbons, aryl groups, alkylaryl groups and alkoxyl groups, and where m=0–2.

In another aspect of the invention, a method for using a Grignard reagent includes introducing a Grignard reagent into a solvent comprising a solvent moiety having a pendant group attached thereto, the pendant group having the formula, —$(CH_2)_m$—OR, where R is selected from the group consisting of linear, branched and cyclic alkyl groups having one to twenty carbons, aryl, alkylaryl groups, and alkoxyl groups, and where m=0–2.

In yet another aspect of the invention, a method for minimizing entry of solvents into the environment in a chemical reaction for which tetrahydrofuran or diethyl ether may be used as a solvent includes using as a solvent a compound selected from the group consisting of:

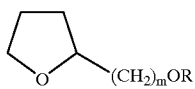

(I)

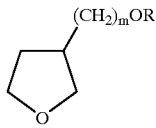

(II)

where R is selected from the group consisting of linear, branched or cyclic alkyl groups having between one and twenty carbons, aryl groups, alkylaryl groups or alkoxyl groups, and where m=0–2. The method may alternatively include using as a solvent a compound comprising a solvent moiety having a pendant group attached thereto, the pendant group having the formula, —$(CH_2)_m$—OR, where R is selected from the group consisting of linear, branched or cyclic alkyl groups having between one and twenty carbons, aryl groups, alkylaryl groups or alkoxyl groups, and where m=0–2. The method may alternatively include using as a solvent a polymer-immobilized solvent, comprising a flexible polymer backbone; and a plurality of pendant groups attached onto the polymer backbone, the pendant groups comprising a flexible linking unit bound to the polymer backbone and to a terminal solvating moiety.

By "solvent" or "solvent moiety", as those terms are used herein it is meant the moiety or molecule which preferentially interacts with the reactants of the chemical or pharmaceutical reaction of interest to provide a suitable microenvironment for the reaction. The "solvent moiety" is a derivative of a selected solvent molecule which makes up a portion of the polymer-immobilized solvent.

By "benign phase or medium", as that term is used herein, it is meant a liquid phase added to the solvents of the present invention which is capable of rendering the solvent of the invention soluble therein. In the case of the polymer-immobilized solvent, only the polymeric backbone may be soluble therein. The medium or liquid phase added is "benign" relative to the solvents for which replacement solvents are sought, i.e., THF, methylene chloride, etc. in the sense that they are less toxic, less volatile, less water soluble and less likely to enter the environment.

The replacement solvents of the present invention which are based upon substituted THF ethers are well suited for use in reaction involving Grignard reagents, metal hydrides, acid chloride addition to amines, methylation reactions, alkali metals (Li, Na, K) and alkaline earths (Mg) in which the coordinating ability of the ether solvent is important to its the reagent's stability and reactivity.

BRIEF DESCRIPTION OF THE DRAWING

The description of the invention is made with reference to the drawings, which are presented for the purposes of illustration only and are in no way intended to be limiting of the invention, and in which.

DETAILED DESCRIPTION OF THE INVENTION

The present invention provides a new class of solvents having solvation properties similar to those currently in use, but which are substantially non-volatile and which can easily be recovered from process streams using simple readily available separations techniques. These novel solvents are obtained by immobilizing a solvent moiety by attachment to flexible polymer backbones. In certain embodiments, it may be possible to use the polymer-immobilized solvent as a neat liquid. Alternatively, the polymers may be dissolved in a more benign continuous phase. The polymer-immobilized solvents may form micelles in the benign phase thereby localizing the solvent moiety within the micellar cores, or the pendant solvent moieties may provide the requisite solvation environments.

The present invention also provides a new class of substituted tetrahydrofuiiuryl ethers and tetrahydro-3-furan ethers which have solvation properties similar to and in some respects better than tetrahydrofuran (THF) or diethyl ether, the solvent for which it may be used as a replacement. The substituted tetrahydrofurfuryl ethers of the present invention are significantly less volatile than THF, are less water soluble or are water immiscible. In addition, they may be easily separated from the reaction solvent train. The present invention has discovered a surprising new use for these molecules and has prepared previously unknown derivatives thereof which are surprisingly useful as solvent replacements.

The description of the invention is directed to the development of replacement solvents for synthetic reaction processes. It is emphasized, however, that the overall scope of this invention includes solvents suitable as replacement solvents for other potential industrial applications as well, applications in which pollution can be readily minimized by appropriate solvent replacement. Indeed, an important part of the invention may be identification of other environmental problems associated with solvent usage, and development of solutions to some of these problems using the concepts described in this proposal.

Figure 1:
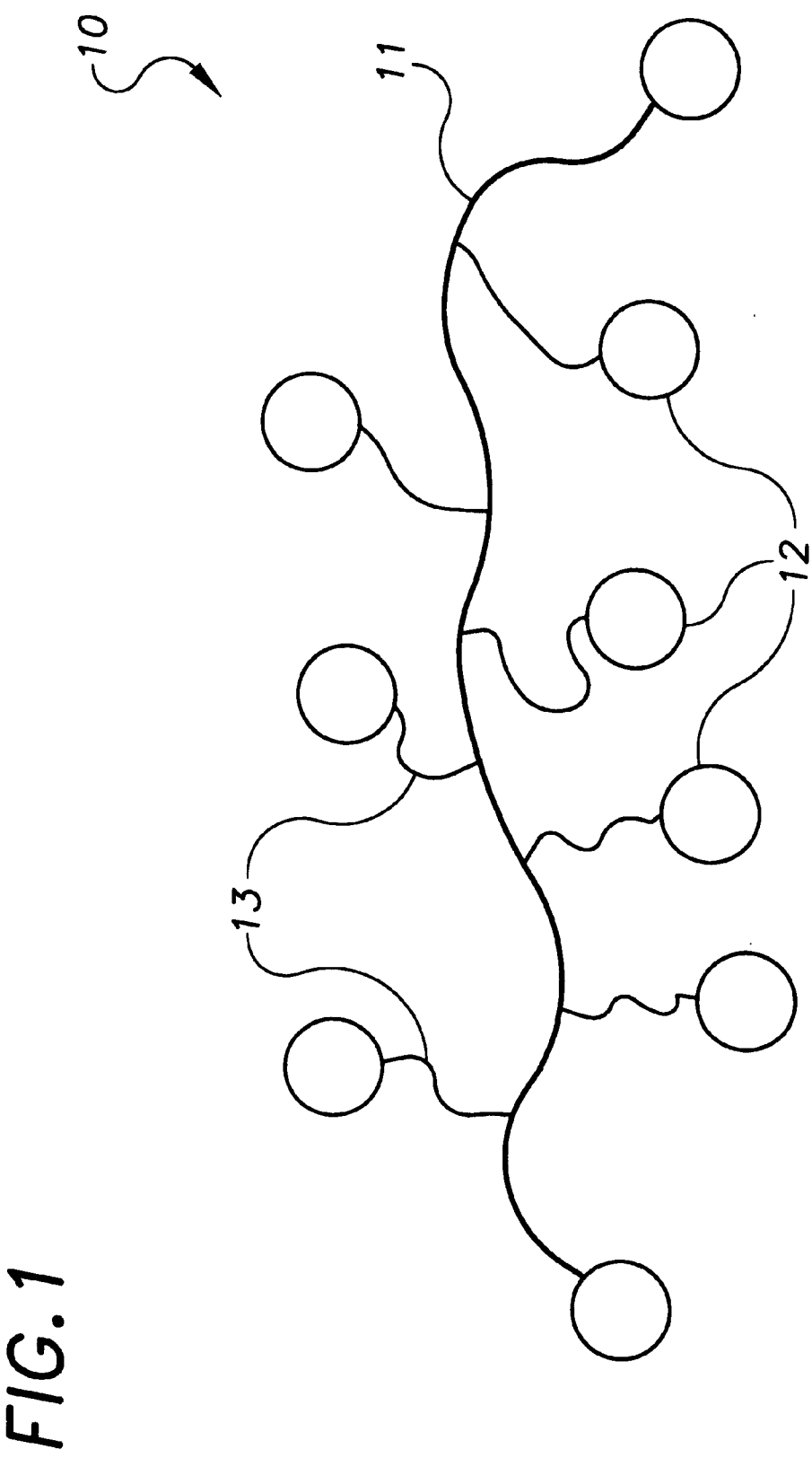
FIG. 1 is a schematic illustration of the polymer-immobilized solvent of the present invention.

The polymer-immobilized solvent of the invention is schematically illustrated in FIG. 1. A polymer-immobilized solvent 10 possesses a flexible Polymer backbone 11. Solvent moieties 12 are bound to the polymer backbone 11 via a flexible linking unit 13. The polymer-immobilized solvent advantageously is (a) soluble in a relatively benign continuous phase, preferably a solvent used in the separation of the product such as the recrystallization solvent of the next solvent to be used in the reaction scheme, (b) able to provide the requisite solvation environment for the reaction, (c) chemically inert to reactions of interest, (d) non-water soluble, and (e) readily separable using mechanical separations such as ultrafiltration instead of energy-intensive distillation processes used for conventional solvents.

In a preferred embodiment, the polymer backbone is inert, that is, it does not interact or participate in the chemical, industrial or pharmaceutical processes for which it is being used. The polymer may be a hydrocarbon-, chlorocarbon- or fluorocarbon-based polymer, prepared from the polymerization of monomers such as olefins, vinyl chloride, vinyl benzene (styrene) and other substituted olefins. Particularly preferred monomers include styrene, 3-vinyl benzyl halides, which also have the potential to be polymerized anionically, thereby providing a route for a relatively monodisperse product. Suitable polymeric backbones include, but are in no way limited to polyethylenic backbones, polypropylenic backbones, polyvinylbenzene-based backbones or polyvinylchloride-based backbones.

Some substitution of the backbone may be permitted. The substitution may be used as the flexible linking unit or a portion thereof. Additional backbone substitution may be selected for improved solubility of the polymer backbone in the benign medium. Thus, the polymeric backbone may be substituted by alkyl, aryl or arylalkyl groups.

The polymer backbone may be a homopolymer or a copolymer or a block copolymer of the monomers and polymers listed herein. The polymer backbone may be linear, branched or a star or comb polymer. It may be desirable in some embodiments to prepare block co-polymers of pendant substituted monomers with additional monomers having desirable solubility properties, so that the resultant polymer may be readily dispersed in non-polar mediums.

The solvent moiety is a moiety which has solvating properties suitable for use in the chemical reaction of choice. The solvent moiety is typically based upon conventional solvents, such as, THF, acetone, MEK, benzene, toluene, methylene chloride, esters, amines and ethers. The solvent moiety may also be polar moieties which are not liquid, but which are known to dissolve in a benign medium, such as crown ethers and cryptands. Suitable ether solvents, for which solvent moieties may be prepared, include, but are in no way limited to $CH_3OCH_2CH_2OCH_3$, (1,2-dimethoxyethane), $CH_3OCH_2CH_2OCH_2CH_2OCH_3$, and $CH_3OCH_2CH_2OCH_2CH_2OCH_2CH_2OCH_3$.

The flexible linking unit links the solvent moiety to the polymer backbone. The flexible unit permits greater freedom of movement for the solvent moiety allowing it to freely interact and to solvate the reactants as the reaction progresses. As for the polymer backbone, the flexible linking unit may be inert to the chemical reaction and non-interactive with the reactants. However, the flexible linkage may have some solubilizing properties, particularly when it is an alkylene oxide linkage such as $(—O(CH_2)_m)_n$. The flexible unit may be on the order of about three to twenty carbon lengths in order to provide suitable freedom of movement for the solvent moiety and to avoid steric encumbrances with the polymer backbone. Suitable flexible units are alkyl, alkyl aryl, aryl, chloroalkyl, or ether linkages. By way of example, the flexible linking unit may be a linear alkyl group, such as ethyl, propyl, butyl, hexyl and the like; an alkyl aryl, such as benzyl, benzyl ether, and the like; or an ether, such as $CH_3OCH_2CH_2OCH_2$— (1,2-dimethoxyethyl), $CH_3OCH_2CH_2OCH_2CH_2OCH_2$, and $CH_3OCH_2CH_2OCH_2CH_2OCH_2CH_2$ $OCH_2$—, and the like.

In one embodiment, the polymer-immobilized solvent includes a polymer backbone derived from polymerization of styrene, and includes a tetrahydrofuran ether solvent moiety attached to the aryl linking unit. Other examples are polymer backbones derived from 3-vinyl benzyl halides, vinyl chloride, alkyl chloride and 1-bromo-8-octene solvent moieties of interest are analogs of toluene, methylene chloride, alcohols and ketones (see, Example 1).

The polymer-immobilized solvent may be a liquid, particularly when the polymer backbone is comprised of very few monomer units. More typically, however, the polymer-immobilized solvent will be a solid. It is then desirable to disperse the polymer solvent in a benign medium. The liquid polymer-immobilized solvent may also be dispersed in a benign medium. Suitable benign mediums include hydrocarbons, such aromatics and alkanes. Suitable alkanes include pentane, hexane, heptane, decane, dodecane, and the like. Suitable aromatics include toluene and the like. The benign medium is desirably inert to the reactant of the chemical process, yet capable of rendering the polymer-immobilized solvent soluble in the benign medium. The benign medium is desirably water immiscible and therefore does not present significant separations problems in the downstream separations operations.

The benign hydrocarbon medium may be used in a range of about 1 to 95% v/v in the solvent mixture, the actual solvent to benign medium ratio being dependent upon the particular chemical reaction. In some instance, very small amounts (ca. 5% v/v) of the polymer-immobilized solvent are sufficient in order to obtain its desired solubilizing effects during the chemical reaction. It is hypothesized that this effect is observed in some cases because the benign medium "concentrates" the more polar solvent moieties, perhaps in micelles, creating an elevated effective concentration of the solvent moieties capable of interacting with the chemical reactants.

An advantage of the benign medium is to contribute to and simplify product separation. When a non-polar hydrocarbon is used as the benign phase, it may promote separation by inducing product crystallization. This has a significant industrial appeal, in that it reduces the need to switch solvents during processing. The separation is further simplified by the immiscibility of the polymer-immobilized solvent in water. Addition of water may cause the polymer to precipitate from the benign medium, which could be advantageous for recovery removal of the polymer solvent from the product.

Figure 2A:
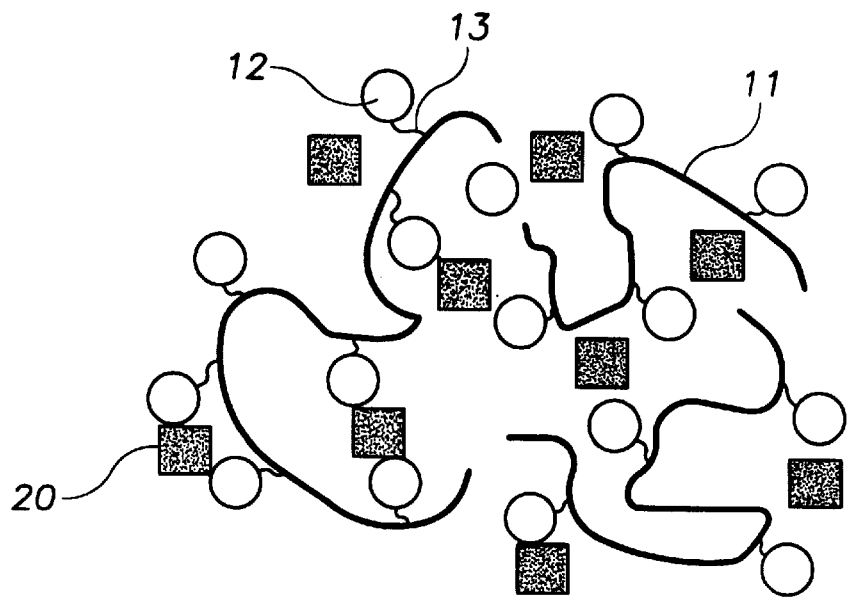
FIG. 2 is a schematic illustration of solvation modes for the polymer-immobilized solvent (a) as a random coils and (b) aggregated to form a micelle.
Figure 2B:
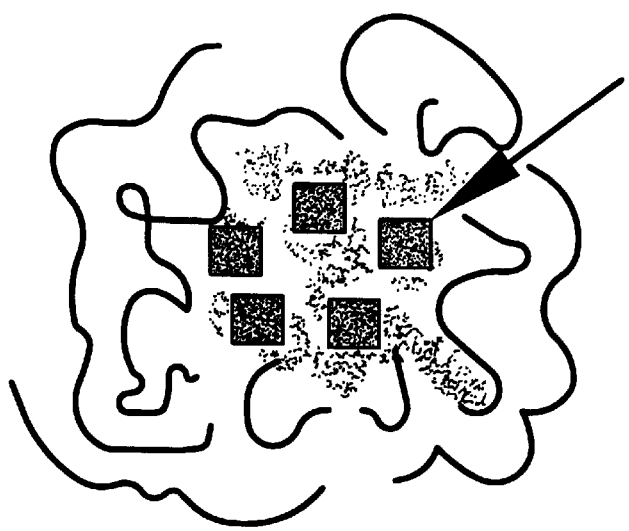

While not being bound to any particular mode of solvation, possible modes of solvation for the polymer immobilized solvent are illustrated in FIG. 2. With reference to FIG. 2(a), the polymer backbones form random coils in neat solution or in solution of an inert solvent. The solvent moieties are therefore free to interact with the solute and form the requisite solvation environments. Alternatively, the polymer may be designed to form monomolecular micelles or may self-assemble to form conventional micelles, as is illustrated in FIG. 2(b). The solvent moieties may be localized within the micelle interior to provide the requisite solvation environment.

A particular advantage to the polymer-immobilized solvents of the present invention is the ability to separate them from the reaction train using readily available and inexpensive techniques. The polymer solvent is no longer water miscible or volatile, but may be easily separated using precipitation, evaporation of the benign medium or filtration. A preferred method of separation includes ultrafiltration. In instances where ultrafiltration is used to separate the polymer immobilized solvent, it is desirable that the polymer have a molecular weight greater than 10,000. Comb and star polymer derivatives are expected to be particularly easy to separate by ultrafiltration. Reverse osmosis may also be suitable, particularly for low molecular weight polymers and oligomers.

In another embodiment, the polymer may coat or comprise a bead to which the pendant group comprising the flexible linking unit and the solvent moiety are attached. The beads may be on the macro-, micro- or nanoscale and hence may be readily removed from the reaction train. The beads may contain a magnetic component which could enable them to be easily removed using a magnetic field.

The polymer-immobilized solvents may be prepared by synthesis of an appropriately functionalized monomer to obtain a "macro monomer" which may then be polymerized using conventional methods to obtain the product polymer-immobilized polymer of the invention. Alternatively, a readily available polymer may be functionalized with the pendant group of the immobilized solvent of the invention. Alternatively, suitable monomers may be polymerized to provide a polymer intermediate. The polymer may be functionalized with the desired flexible linking unit and solvent moieties. Such an approach may not result in uniform distribution of pendant groups along the polymer backbone. It may nonetheless be an attractive alternative in systems which have no readily accessible functionalized monomers. Yet another possible reaction scheme is to attach the solvent moiety to the termini of highly branched polymers, such as star polymers. The interested reader is directed to *Polymer Synthesis*, 2nd revised ed., Paul Rempp and Edward W. Merrill, Eds. Huthig & Wepf, Verlag N.Y. (1991) for further information on polymer synthesis.

The polymer backbone may be prepared as a copolymer. In one embodiment, the polymer backbone may be comprised of block copolymers, one of which is compatible with the benign medium, and the other which is not. The polymer block incompatible with the benign medium includes the pendant solvent moiety. It is expected that the hydrocarbon-compatible copolymer block will extend into the benign medium, whereas the incompatible copolymer block will be concentrated into a micelle core, shielded from the inert medium. In another embodiment, monomers which are not especially reactive to polymerization may be copolymerized free radically with more reactive monomers. Examples of preferred monomers for a polymer-immobilized solvent, which do not readily homopolymerize include, 8-octene tetrahydrofurfuryl ether, 8-octene tetrahydro-3-furan methane ether, 2-propene tetrahydrofurfuryl ether, and 2-propene tetrahydro-3-furan methane ether. These monomers, however, possess desirable pendant groups for the immobilized solvent. The monomers may be copolymerized with reactive monomers, such as styrene and styrenic tetrahydrofurfuryl ether, to form the polymer of the present invention.

A new class of substituted tetrahydrofurfuryl ethers and substituted tetrahydro-3-furan ethers has also been designed and synthesized and shown to be as effective as THF in particular pharmaceutical reaction schemes. These solvents have the structure (I) or (II):

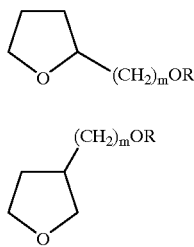

where m=0–2. R is a linear, branched or cyclic alkyl group having between one and twenty carbons, an aryl group, an alkylaryl group or an alkoxyl group having up to 20, and preferably 10, ether linkages. Suitable alkyl groups include, by way of example only, butyl, isobutyl, hexyl, octyl, decyl, cyclohexyl, and the like. Suitable aryl groups include benzyl, ethyl benzyl and the like. Suitable ether groups include $CH_3OCH_2CH_2OCH_2$— (1,2-dimethoxyethyl), $CH_3OCH_2CH_2OCH_2CH_2OCH_2$— (diglyme), and $CH_3OCH_2CH_2OCH_2CH_2OCH_2CH_2OCH_2$— (triglyme), and the like.

n-Octyl tetrahydrofurfuryl ether (nOTE), where m=1, is particularly preferred because of its ease of manufacture, low volatility (b.p.=239° C.) and low water immiscibility. The higher order alkyl derivatives are particularly of interest as replacement solvents because of their increased boiling points and water immiscibility. The pendant ether linkage is particularly desirably because it is highly flexible, adds additional solvating capability and does not restrict the freedom of movement of the attached THF molecule. The 2-substituted and 3-substituted derivatives designated by structures (I) and (II) are referred to herein as "2-alkyl THF ethers" and "3-alkyl THF ethers", respectively.

The alkyl tetrahydrofurfuryl ethers may be prepared by reaction of the tetrahydrofurfuryl alcohol with stoichiometric quantities of the appropriate alkyl chloride using sodium hydroxide. Because of the reduced reactivity of the three-position alcohol starting material, a more reactive base is used in the reaction. The higher cost of the starting materials in the manufacture of the 3-position alkyl THF ether will be a factor for industrial scale-up of the process. The two-position alkyl THF ethers may be preferred for industrial applications. Table 1 reports on the derivatives and their properties. In Table 1, the nomenclature "2-butyl" indicates substitution at the 2-position on the furan ring by a butyl group. Boiling points for all alkyl THF ether derivatives increase significantly; freezing point is less than –60° C. in all cases, so that all solvents are within practical working range for industrial use.

TABLE 1

Properties of various alkyl THF ethers

| Solvent | Freezing Point (° C.) | Boiling Point (° C.) | Viscosity (cP) | | |
|---|---|---|---|---|---|
| | | | 15° C. | 25° C. | 35° C. |
| THF | –108 | 65.4 | 0.57 | 0.56 | — |
| 2-butyl | <–80 | 168 | 1.88 | 1.73 | 1.38 |

TABLE 1-continued

Properties of various alkyl THF ethers

| Solvent | Freezing Point (° C.) | Boiling Point (° C.) | Viscosity (cP) | | |
|---|---|---|---|---|---|
| | | | 15° C. | 25° C. | 35° C. |
| 2-hexyl | <–80 | 225 | 2.86 | 2.70 | 1.88 |
| 2-octyl | –62 | 239 | 4.17 | 3.76 | 2.65 |
| 3-butyl | <–80 | 194 | 2.10 | 1.91 | 1.55 |
| 3-octyl | –60 | 229 | 4.65 | 4.12 | 3.03 |

Substituted THF ethers may also be dispersed in a benign medium for use in chemical reactions. Suitable benign mediums include those listed above for the polymer-immobilized solvents. Hydrocarbon/substituted THF ether mixtures may have solution properties which make them better solvents than THF alone. This is demonstrated by fluorescence measurements on THF, 2-alkyl THF ethers, 3-alkyl THF ethers and mixtures with hexane. Fluorescence spectroscopy may be used to determine the local micro viscosity and polarity of a solution. Pyrene for example is a spectroscopic probe which is sensitive to the polarity of the medium in which it is dissolved. Pyrene exhibits a characteristic fluorescence emission spectrum consisting of mainly five bands that are referred to as $I_1$ through $I_5$. The $I_1/I_3$ intensity ratio depends strongly on the polarity of the medium; the larger the ratio, the more polar the medium.

Figure 3:
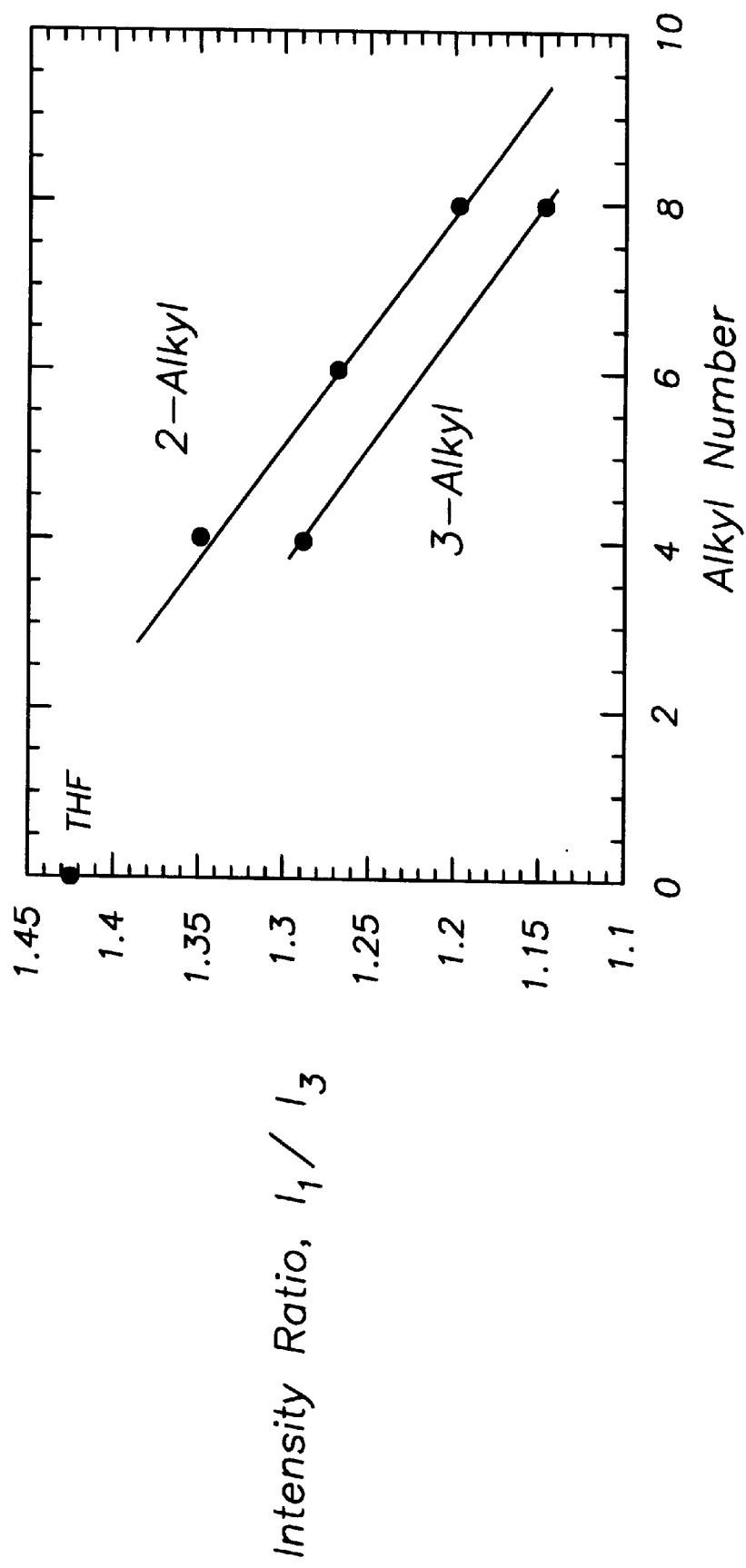
FIG. 3 is a plot of pyrene $I_1/I_3$ ratios for THF and a series of 2-alkyl and 3-alkyl THF ethers.
Figure 4:
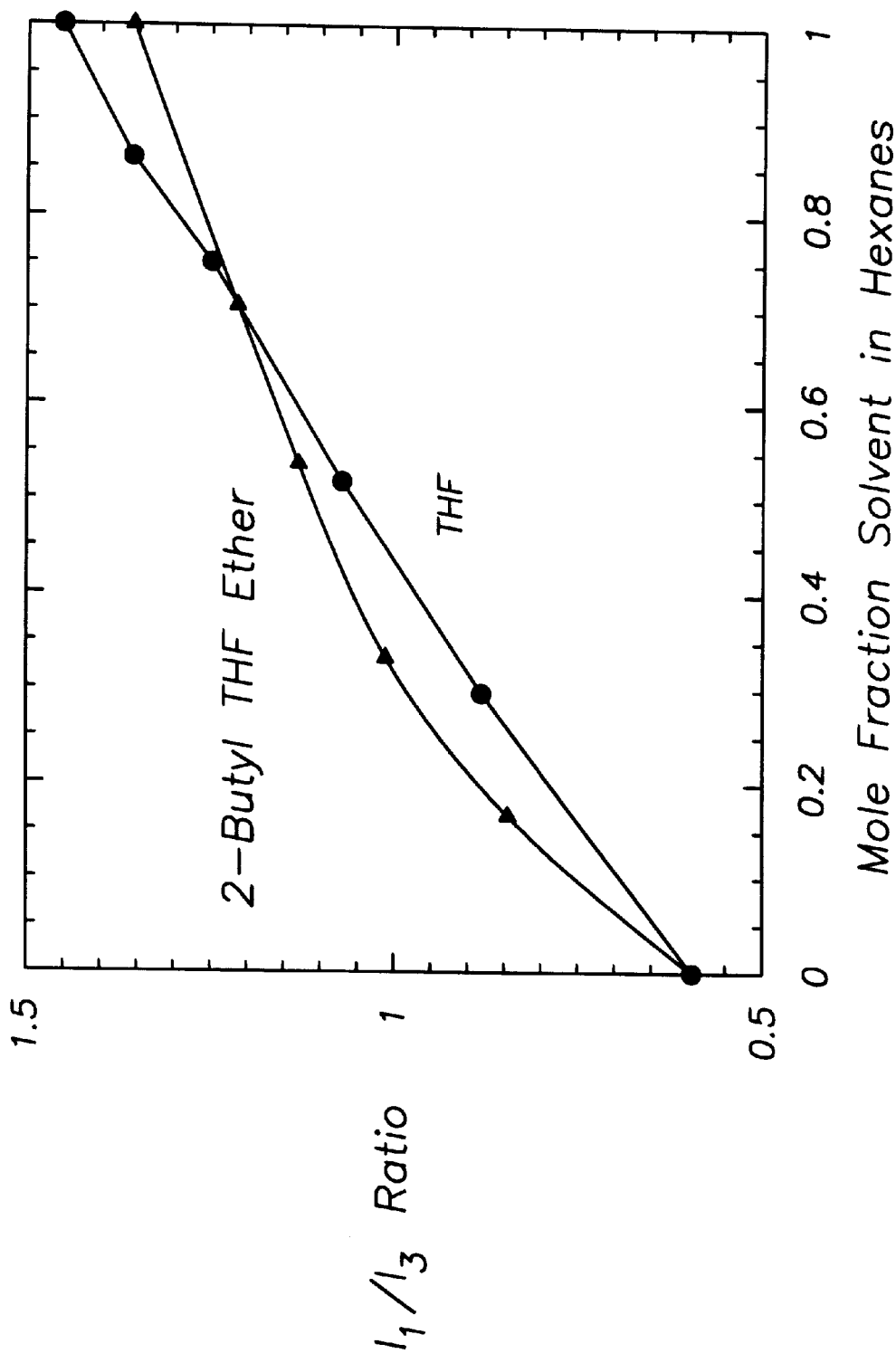
FIG. 4 is a plot of pyrene $I_1/I_3$ ratios for THF and 2-butyl THF ether in varying amounts of hexane.

FIG. 3 shows the pyrene $I_1/I_3$ ratio for THF, 2-alkyl THF ethers and 3-alkyl THF ethers of varying alkyl lengths. Not surprisingly, the substituted THF ethers were less polar than unsubstituted THF, with polarity decreasing with increasing alkyl chain length. This result is compared to the pyrene $I_1/I_3$ ratios shown in FIG. 4 for THF/hexane and 2-butyl THF ether/hexane mixtures. THF exhibited a linear response throughout the entire solvent range. 2-Butyl THF ether, however, showed a non-linear response, with greater polarity than THF in low hexane mole fractions and a lower polarity than THF in high hexane mixtures. This observation supports the model of a solvent system in which the polar solvent moieties are clustered, or aggregated in micelle form, where they may have optimal interaction with the reagents of a chemical reaction. This phenomenon in a non-polar hydrocarbon medium may be particularly significant for use of the polymer-immobilized solvent, where it may not be possible to use large volume or molar fractions of the polymer-immobilized solvent.

In order to demonstrate the efficacy and utility of these new solvent systems, the solvents of the present invention were used as a solvent in a reaction of interest to the pharmaceutical industry. It is known, for example, that the ether linkage present in THF plays an important role in the formation and stability of Grignard reagents and that preparation of Grignard reagents in non-ethereal solvents is difficult.

Figure 5:
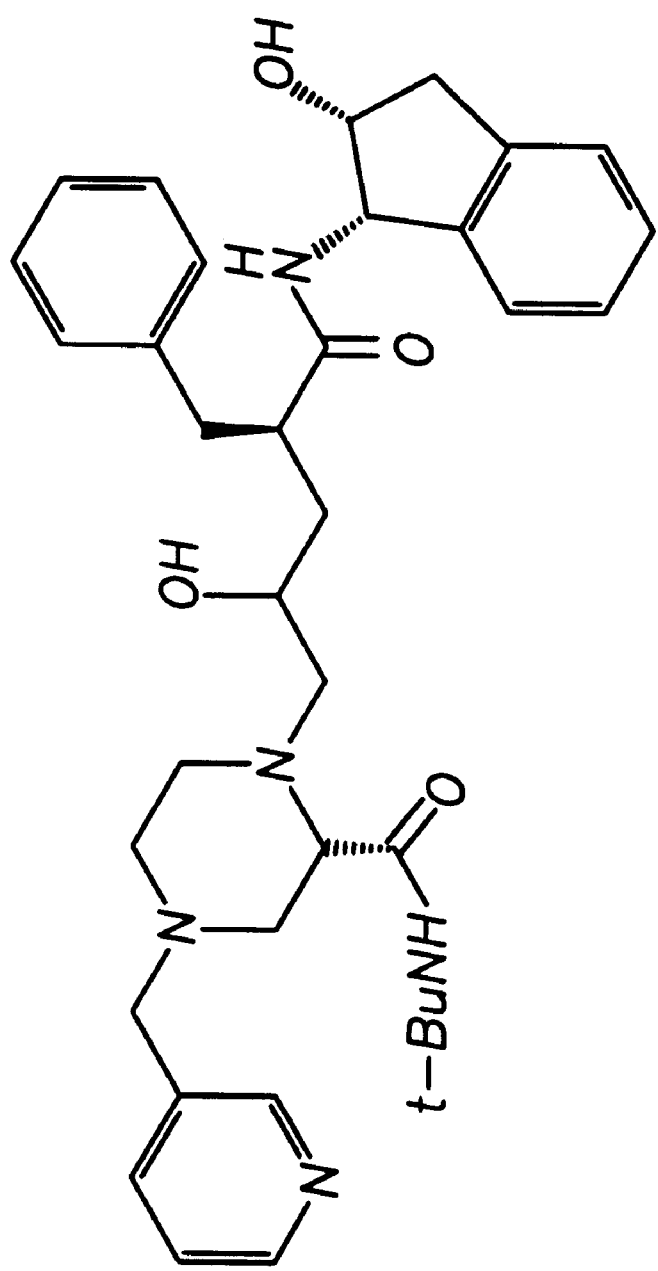
FIG. 5 is an illustration of the chemical structure of HIV-1 protease inhibitor, commercially available as Indinaviro® and Crixivan®.

The reaction identified for testing included a series of reactions leading to a key intermediate in the synthesis of an orally active HIV-1 protease inhibitor, Merck's L-723,524, available as Indinavir® or Crixivan® (FIG. 5). Because therapeutic doses of this drug are in the gram quantities and it contains several chiral centers, it has been a hugh challenge for the pharmaceutical industry to synthesize up to one million kilograms per year. The reaction sequence that was investigated is shown in eq. 1.

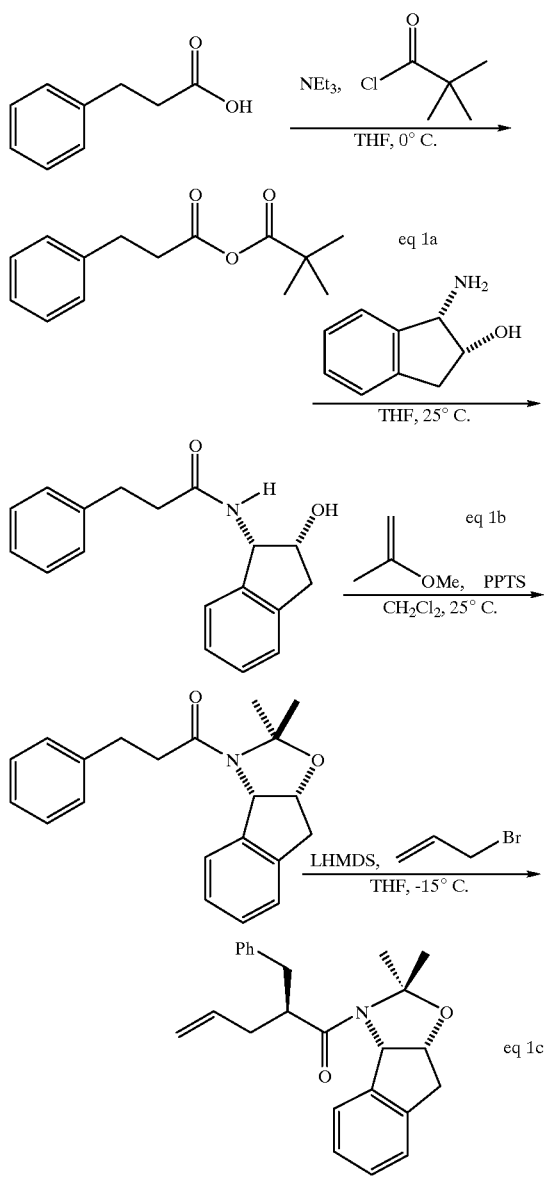

In the published literature, hydrocinnamic was first dissolved in dry THF and then triethylaminse was added followed by pivaloyl chloride to form the amide. The amino-alcohol, slurried in THF, was then added to the reaction mixture, and was subsequently partitioned between water and ethyl acetate during sodium bicarbonate and sodium sulfate washings. The intermediate solution was then concentrated in vacuo. In the usual case, any THF not lost to the water phase was removed under vacuum. The crude amide was then slurried in methylene chloride. To this suspension was added the 2-methoxy propene followed by the pyridinium p-toluene sulfonate. This solution was then poured into saturated aqueous sodium bicarbonate for partitioning and the aqueous phase was extracted with methylene chloride. The volatiles were removed in vacuo to afford the crude product which was dissolved in THF for recrystallization with hexane. The yields for these reactions were generally about 60–65%. The thus-obtained amide acetonide crystals were dissolved in THF solution of allyl bromide and lithium hexamethyldisilazide (LHMDS; made in THF from n-butyl lithium and hexamethyldisilazane (HMDS)) to form the allylated acetonide. See, Askin et al. *J. Org. Chem.* 57:2771 (1992) and Askin et al. *Tetraberon Lett.* 35:673 (1994).

The present invention demonstrates that, in the reaction sequence set forth hereinabove, solvent switches and the accompanying need for solvent separation and recovery may be eliminated using nOTE as the solvent. The complexity of the overall process and the high energy costs associated with the many separation steps are avoided, as well as many of the possible opportunities for environmental contamination. Loss of nOTE to the water phase during separation, work-up and vacuum separation is very minor. nOTE can also serve as the extraction solvent instead of ethyl acetate or methylene chloride for separation of the intermediate products. Advantageously, nOTE can be used throughout the entire reaction sequence, thereby avoiding costly solvent switches and reducing solvent requirements. As a further advantage, it was not necessary to crystallize and isolate the amide acetonide product from nOTE, as is required in a THF solution. Instead, LHMDS (prepared in nOTE from n-butyl lithium and HMDS) was added directly to the reaction mixture without the need for drying the mixture, since nOTE has a low capacity for water. The allylated acetonide product was recrystallized from the reaction mixture by addition of hexane. The product was characterized by spectroscopic methods and its purity was determined by elemental analysis. The overall yield of the allylated acetonide product for this three-step process was the same as obtained in THF; however, nOTE may also be recovered directly. After crystallization and filtration, the replacement solvent is readily recovered by distillation. In this manner, approximately 95% of the reusable replacement solvent may be recovered on a laboratory scale. Recovery on a process scale is expected to be much higher.

Figure 6:
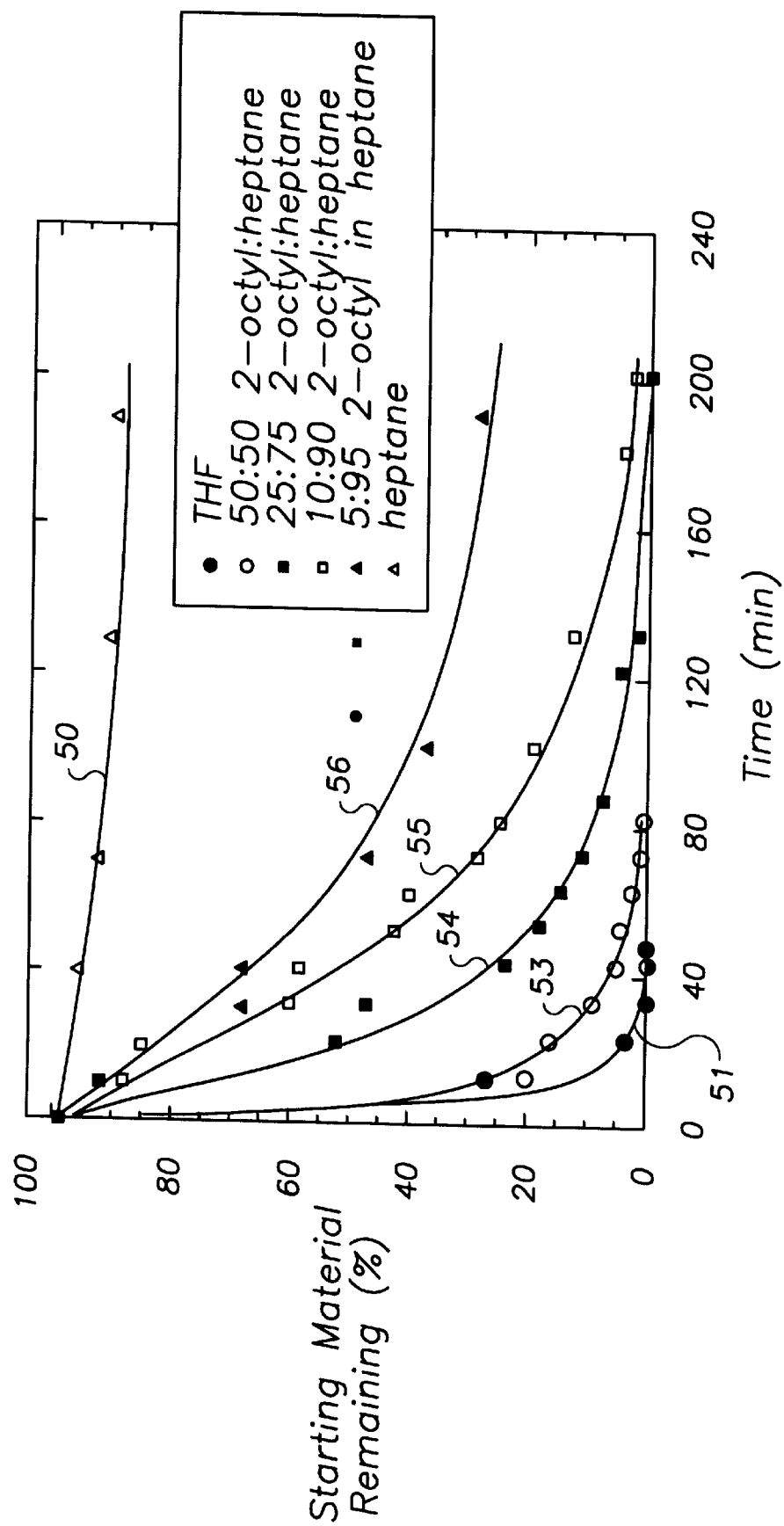
FIG. 6 is a graph showing reaction kinetics for the model reaction in 2-alkyl THF ether solvents.

The effect of replacement solvents on reaction rate was also investigated. For this investigation, the allylation step shown in eq. 1c was examined. The allylation step was previously deemed to proceed only in the THF or diethyl ether solvent. Thus the allylation step was used as a test system for the efficacy of the replacement solvents of the invention (see, Example 4). The extent of reaction for the model reaction was monitored in the alkyl THF ether solvents and alkyl THF ether/heptane solvent mixtures of the invention. The results are reported in FIG. 6. The reaction in neat heptane (curve 50) and neat THF (curve 51) were used as controls and indicate that the reaction does not progress in heptane and is complete within about an hour in THF. Neat 2-octyl THF ether (curve 52) and 50:50 2-octyl THF ether:heptane (curve 53) were also complete within about an hour. Thus, they are comparable replacement solvents for the model reaction. Reactions carried out in 25:75, 10:90,and 5:95 2-octyl THF ether:heptane (curves 54, 55, 56, respectively) also promoted the reaction, although the time to completion was greater.

Figure 7:
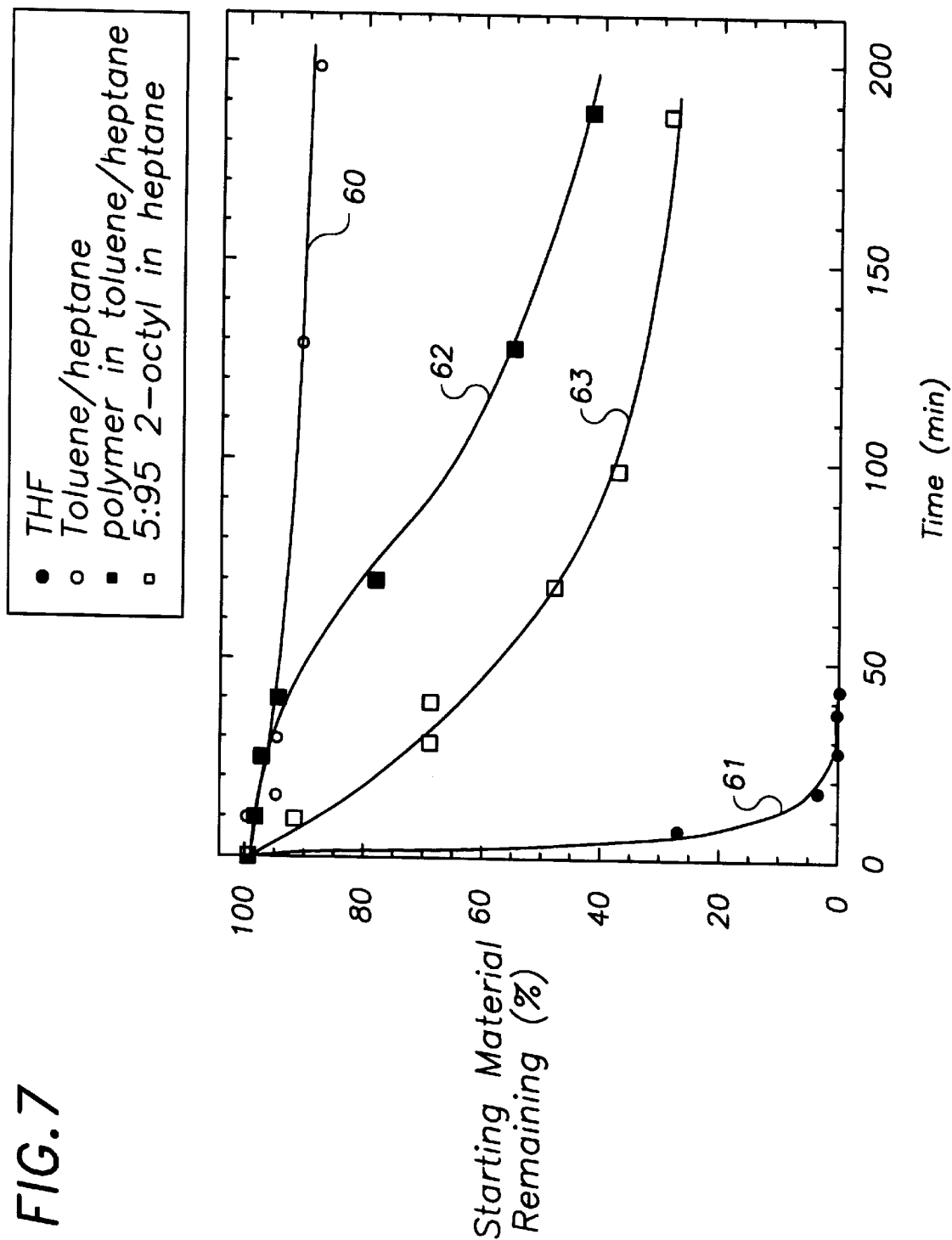
FIG. 7 is a graph showing reaction kinetics for the model reaction in polystyrenic-immobilized solvents.

The extent of reaction for the model reaction was monitored for the polystyrenic-tetrahydrofuran ether/heptane/toluene solvent mixture of the invention (see, Example 1). The reaction was carried out in a toluene/heptane mixture because the polymeric solvent is not soluble in heptane. The results are reported in FIG. 7. Heptane:toluene (curve 60) and neat THF (curve 61) were used as controls and indicate that the reaction does not progress in heptane:toluene and is complete within about an hour in THF. When the polymeric solvent is used in very small concentrations (0.1 g/mL), the reaction went to 50% completion in just 2 hours. The polystyrenic-tetrahydrofuran ether/heptane/toluene solvent mixture was prepared at a concentration of 0.25 g polymer/5 mL heptane:toluene mixture, which is comparable in vol fraction solvent to a 5:95 alkyl THF ether in heptane mixture. The performance of the polystyrenic-tetrahydrofuran ether/heptane/toluene solvent mixture is shown as curve 62 and is compared to the performance of the comparable 5:95 alkyl THF ether in heptane mixture (curve 63), indicating that the two solvent systems show comparable effects on the reaction kinetics of the model reaction.

Advantageously, the polymer-immobilized solvent used in the above model reaction was not lost to the water phase during work-up. Still advantageously, the polymer may be removed from the reaction mixture by ultrafiltration (see, Example 6). The reaction products and any excess reagents are thereby separated from the polymer and remain in the toluene diluent. The product may then be separated by recrystallization or carried on to the next step in the reaction scheme. Thus, a single reaction solution (polymer-immobilized solvent+diluent) may be used for two or more steps in the reaction sequence. The polymer-immobilized solvent may be washed with a non-solvent (e.g., hexane) and recovered by ultrafiltration for reuse. More than 95% of the polymer-immobilized solvent has been recovered in the present system in this manner. It is anticipated that large-scale processing would improve recovery rates.

The replacement solvents of the present invention may be selected to be asymmetric. Thus, in reactions involving chiral, or asymmetric centers, a particular stereoisomer may be favored. The advantages of minimized entry into the environment and simplified separations processes would apply.

The replacement solvents provide simplification of the reaction, extraction and isolation sequences used in pharmaceutical and chemical synthesis. An example of how the replacement solvents of the invention may be used in chemical processes includes the steps of (1) reaction, in which a reaction is carried out in a polymer-immobilized solvent/hexanes mixture (or water immiscible alkyl THF ether/heptanes mixture) that behaves like THF; (2) extraction, in which the reaction mixture is extracted with water and the salts and polar substituents are removed while the product is retained within the solvent phase; and (3) isolation, in which a temperature shift is applied causing the solvent to "expel" the product which then crystallizes in the hexanes. Thus the two solvents currently used could be replaced by a single replacement solvent system.

The invention is described with reference to the following examples which are presented for the purpose of illustration only and which are no way intended to be limiting of the invention.

EXAMPLE 1

Synthesis of Styrene-immobilized Tetrahydrofurfuryl Ether.

The polymeric solvent is prepared according to the following reaction scheme (2).

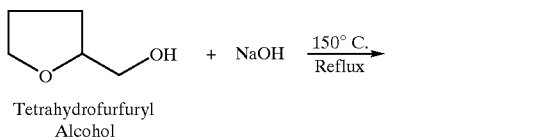

(2)

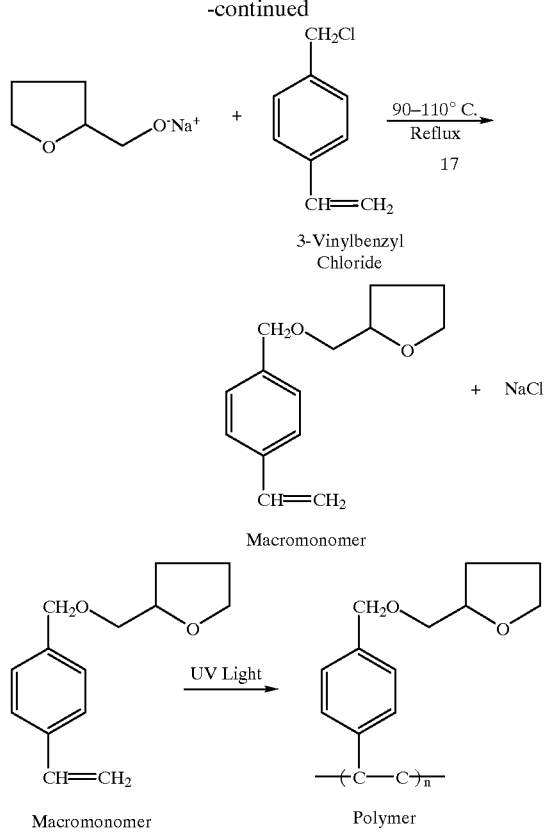

The styrene based monomer is made from commercially available 3-vinylbenzyl chloride (3-(chloromethyl) styrene) by first activating the tetrahydrofurfuryl alcohol with sodium hydride and then adding the 3-vinylbenzyl chloride dropwise to the solution and allowing the solution to reflux overnight at 70° C. This THF derivatized styrene monomer was then polymerized by free radical polymerization using 0.1 mole percent benzoyl peroxide and refluxing at 85° C. Solvent is not necessary for the polymerization reaction. The polymerization can be controlled using methanol and diethyl ether is used to separate unreacted monomer and low molecular weight oligomers. Gel permeation chromatography (GPC) showed a broad molecular weight distribution (PDI=4), 4000 to 20,000 g/mole. In other synthesis, the poly(3-vinylbenzyl tetrahydrofurfuryl ether) produced had a number average molecular weight of 11,600 g/mol and a weight average molecular weight of 21,400 g/mol (PDI= 1.84). The resulting polymer is soluble in a 1:1 mixture of toluene:heptane and toluene.

A known weight of polymer was transferred to an Aldrich®sure-seal bottle in a glove box. The polymer was then diluted with dry toluene to make a 20 w/w % stock solution to use in the testing of the model reaction as described herein.

EXAMPLE 2

Synthesis of n-alkyl Tetrahydrofurfuryl Ether.

The n-butyl, n-hexyl, and n-octyl ethers were synthesized according to this reaction. Tetrahydrofurfuryl alcohol (THFA) was activated with NaOH pellets by refluxing at 150° C. The mixture was cooled to 90–100° C. before dropwise addition of 1-chloroalkane. After addition was complete, the mixture was allowed to reflux an additional 2–3 hours and was filtered to remove the NaCl which formed as a byproduct. The filtrate was washed with 100 mL diethyl ether and water was added for separation of the product in a separatory funnel. Several volumes of small washings with the water produced a yellow product which became clear after rotary evaporation of the diethyl ether.

EXAMPLE 3
Synthesis of n-alkyl Tetrahydro-3-furan Methane Ethers

These ethers were prepared in a method similar to that used in Example 2, with the following changes. The different ether substitution on the THF moiety necessitated the use of a stronger base, sodium hydride. Due to the greater expense of the alcohol starting material, THF was used as the solvent instead of excess alcohol. In addition, an alkyl bromide was used to form the ether linkage instead of an alkyl chloride.

As above, 3-substituted THF alcohol was activated with sodium hydride and the appropriate alkyl bromide was added dropwise to the solution and allowed to reflux at 70° C. until the reaction was complete (several hours). The product was worked up as described above. The n-butyl, n-hexyl and n-octyl tetrahydro-3-furan methane ethers were synthesized.

Both the 2-alkyl and 3-alkyl THF ethers were distilled from sodium benzophenone ketyl ether and obtained in greater than 99.5% purity.

EXAMPLE 4
Allylation of Acetonide and Study of the Reaction Kinetics

Both the 2-position and 3-position THF ethers needed to be distilled from sodium benzophenone ether ketyl in order to render them anhydrous for use in the model reactions. The acetonide starting material was made according to supplemental material in *J. Org. Chem.* 57 (10):2772 (1982).

In a dry 100 mL 3-neck flask, equipped with a magnetic stirrer, was placed 5 mL of the replacement solvent to be investigated. To this was added hexamethyldisilazide (HMDS, 0.360 mL, 1.17 mmol). The mixture is cooled to 0° C. and n-butyl lithium was added in a 1:1 mole ratio. The reaction is stirred (ca. ½h) to obtain lithium hexamethyldisilazide (LHMDS).

In a second dry 100 mL flask equipped with a magnetic stirrer was placed 5 mL of the replacement solvent to be investigated. The replacement solvent was mixed with benign solvent in some experiments. For the alkyl THF ethers, heptane was used as the benign solvent. For polymeric THF ethers, a 1:1 mixture of heptane and toluene was used as the benign solvent.

To this, acetonide (0.5 g) was added. When THF is used as the solvent, the acetonide dissolves completely. When the replacement solvents are used, acetonide only partially dissolves, but as acetonide is consumed and the product is formed, more acetonide dissolves into the reaction medium. Since the preparation of LHMDS is usually done in THF, this provides yet another example of the successful use of the replacement solvent.

Allyl bromide was then added (0.14 mL, 1.03:1.0 allyl bromide to acetonide) at room temperature and was cooled to and maintained at −20° C. The LHMDS solution was added over a period of ten minutes. Samples of the reaction mixture were removed at regular intervals and examined by high pressure liquid chromatography (HPLC) to determine the extent of the reaction. The sample was quenched with methanol and citric acid, then diluted with methanol, for injection into the HPLC. When quenched, the polymer THF ether solvent precipitated out of solution and the sample was taken from the supernatant liquid.

EXAMPLE 5
Synthesis of Monomers for Preparation of Polymer-immobilized Solvents Tetrahydrofurfuryl alcohol (THFA) was activated with sodium hydride before dropwise addition of allyl bromide, 1-bromo-8-octene or 3-vinyl benzylchloride. After addition was complete, the mixture was allowed to reflux at 70° C. After workup as in Example 2, the product alkylene tetrahydrofurfuryl ether was obtained. The monomer may be used as a replacement solvent for THF or may then be polymerized to form a polymer-immobilized solvent.

EXAMPLE 6
Ultrafiltration Recovery of Polymer-immobilized Solvent

In the model allylation reaction described herein, quenching of the reaction with a solution of citric acid in methanol caused the polymer-immobilized solvent to form a suspension in solution and this mixture was then microfiltered using a centrifuge (0.1 µm Durapore® filters (Millipore)). Aliquots taken from the model reaction were microfiltered at 4500 rpm for one hour. The polymer was washed with methanol and refiltered. This process was repeated several times to ensure that all of the product and excess reagents are removed from the polymer-immobilized solvent. Hexane, which is a nonsolvent for the polymer-immobilized solvent, was used for final collection of the polymer-immobilized solvent.

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

What is claimed is:

1. A composition, comprising:

one or more reactants, wherein each of the said one or more reactants is a Grignard reagent capable of being solvated by tetrahydrofuran; and a solvent for solvating the one or more reactants, wherein said solvent has the formula,

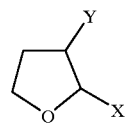

wherein X=(CH$_2$)$_m$OR, Y=H, and m=0–2, or Y=(CH$_2$)$_m$OR, X=H, and m=0–2 such that each occurrence of R is independently selected from the group consisting of aryl, alkylaryl, alkoxyl, linear alkyl, branched alkyl, and cyclic alkyl, wherein when X=(CH$_2$)$_m$OR, said linear alkyl, branched alkyl, and cyclic alkyl groups have six to twenty carbons each, and when Y=(CH$_2$)$_m$OR, said linear alkyl, branched alkyl, and cyclic alkyl groups have one to twenty carbons each.

2. The composition of claim 1, wherein m=1 and R is n-octyl.

3. The composition of claim 1, wherein said linear, branched, or cyclic alkyl group is selected from the group consisting of hexyl, octyl, decyl, and cyclohexyl.

* * * * *